United States Patent [19]

Schulz

[11] 4,051,203

[45] Sept. 27, 1977

[54] METHOD FOR PURIFYING BIDENTATE ORGANOPHOSPHORUS COMPOUNDS

[75] Inventor: Wallace W. Schulz, Richland, Wash.

[73] Assignee: The United States of America as represented by the United States Energy Research and Development Administration, Washington, D.C.

[21] Appl. No.: 703,325

[22] Filed: July 8, 1976

[51] Int. Cl.$^2$ ............................................... C07F 9/32
[52] U.S. Cl. ...................................... 260/990; 210/21; 260/943
[58] Field of Search ................... 260/990, 943; 210/21

[56] References Cited

U.S. PATENT DOCUMENTS

| | | | |
|---|---|---|---|
| 2,710,250 | 6/1955 | Andrews et al. | 210/21 |
| 3,739,047 | 6/1973 | Stanford et al. | 260/990 |

*Primary Examiner*—Richard L. Raymond
*Attorney, Agent, or Firm*—Dean E. Carlson; Frank H. Jackson; James W. Weinberger

[57] ABSTRACT

Bidentate organophosphorus compounds useful for extracting actinide elements from acidic nuclear waste solutions are purified of undesirable acidic impurities by contacting the compounds with ethylene glycol which preferentially extracts the impurities found in technical grade bidentate compounds.

6 Claims, No Drawings

METHOD FOR PURIFYING BIDENTATE ORGANOPHOSPHORUS COMPOUNDS

CONTRACTUAL ORIGIN OF THE INVENTION

The invention described herein was made in the course of, or under, a contract with the UNITED STATES ENERGY RESEARCH AND DEVELOPMENT ADMINISTRATION.

BACKGROUND OF THE INVENTION

The present invention relates to liquid extraction processes and, more particularly, to an improvement in the liquid-liquid extraction process for the recovery and partitioning of actinide values from acidic nuclear reactor waste aqueous solutions using bidentate organophosphorus compounds.

Solvent extraction processes which employ bidentate organophosphorus extractants are presently being actively developed at U.S. Energy Research and Development Administration Facilities in Hanford, Washington, and at Idaho Falls, Idaho, for the removal and recovery of the actinide elements, particularly americium and plutonium, from nitric acid waste solutions generated at these sites. In general, the bidentate organophosphorus compounds are efficient extractants of actinide values which are present in trivalent, tetravalent, and hexavalent oxidation states in the acidic nuclear waste aqueous solutions. With the bidentate extractant, essentially all actinide values, e.g. Am(III), Cm(III), Pu(IV), Np(IV) and U(VI) are extracted into the organic phase and, thereafter, the actinides are selectively stripped into trivalent, tetravalent and hexavalent fractions by contact with dilute aqueous acidic or alkaline solutions. One key feature of these processes is that they involve the use of dilute $HNO_3$ to selectively strip trivalent (Am, Cm) actinides from coextracted tetravalent and hexavalent actinides. U.S. Pat. No. 3,993,728, issued Nov. 23, 1976, describes the application of bidentate organophosphorus extractants in actinide removal schemes from various acid nuclear fuel processing solutions such as those generated in the Purex process.

Currently preferred bidentate extractants are dihexyl-N,N-diethylcarbamylmethylenephosphonate, hereinafter referred to as DHDECMP, and dibutyl-N,N-diethylcarbamylmethylenephosphonate, hereinafter referred to as DBDECMP. These extractants and other neutral bidentate organophosphorus compounds are generally available as crude products which contain various impurities. One of these impurities is an unidentified acidic compound which has a very great affinity for actinide elements at low (e.g. less than 0.25 M $HNO_3$) aqueous phase acidities. Thus, the DHDECMP or DBDECMP extractants must be purified of this acidic component to permit the use of low acid solutions to partition the trivalent actinides, i.e. trivalent amercium, from the other co-extracted actinides.

At present, the only known methods for purifying the commercially available DHDECMP or DBDECMP from the offending unknown acidic contaminant are by vacuum distillation or by contacting the organic extractants with a 6 M HCL solution at 60° C. for 24 to 48 hours and washing the resulting organic phase at 25° C. with equal volume portions of 1 M NaOH, 1 M $HNO_3$ and HO. Both of these purification procedures have a number of disadvantages. Specialized vacuum distillation equipment is expensive and vacuum distilled DHDECMP or DBDECMP would cost more than twice as much as technical grade material. Specialized, corrosion resistant equipment is needed to perform HCL hydrolysis of the bidentate extractants, but more importantly, the HCl also attacks the DHDECMP as well as the acid impurity. Thus the acid hydrolysis procedure requires precise and careful control to produce a satisfactory extractant. Therefore, there is a need for a simple, reliable and inexpensive purification procedure which can be carried out in conventional, stainless steel equipment.

SUMMARY OF THE INVENTION

A simple and effective process has been developed for removing the acidic impurities and improving the extraction properties of technical grade bidentate organophosphorus compounds. By the process of the invention bidentate organophosphorus compounds, diluted in a water-immiscible organic solvent to form an extractant, are contacted with ethylene glycol whereby the impurities are taken up by the ethylene glycol and the purified extractant separated from the ethylene glycol.

It is therefore one object of the invention to provide a simple and effective method for purifying and improving the extraction properties of the bidentate organophosphorus compounds.

It is the other object of the invention to provide a simple and effective method for removing the acidic impurities and improving the extraction properties of technical grade DHDECMP and DBDECMP by contacting the compounds with ethylene glycol.

DESCRIPTION OF THE PREFERRED EMBODIMENT

These and other objects of the invention may be met by diluting the DHDECMP or DBDECMP to about 30 volume percent (v/o) in a water-immiscible organic diluent such as carbon tetrachloride ($CCl_4$), trichlorobenzene (TCB) or n-dodecane to form an extractant, contacting the extractant with three equal volumes of ethylene glycol at about 60° C. whereby the impurities in the extractant are taken up by the ethylene glycol, and separating the purified extractant from the ethylene glycol.

Since the bidentate compounds are completely miscible with ethylene glycol, it is important that they be diluted before the purification process takes place. Satisfactory diluents are any water-immiscible organic compounds in which the bidentates are soluble such as the chlorinated hydrocarbons and the long-chain aliphatic hydrocarbons. $CCl_4$, trichlorobenzene, and n-dodecane have been found especially useful since they form the extractants with the bidentate compounds to recover the actinide elements. The dilution of the bidentates may vary from about 5 to about 40 v/o with about 30 v/o preferred for the actinide extraction process.

Volume ratios of ethylene glycol to bidentate extractant may vary from 1 to 10 to 2 to 1 or greater depending upon the amount of bidentate compound in the diluent. For a 30 v/o bidentate extractant, best results were achieved using a 1 to 1 volume ratio.

The number of contacts between the ethylene glycol and extractant is also dependent upon volume ratios and bidentate dilution. For a 30 v/o bidentate solution using a 1 to 1 volume ratio, a single contact between the extractant and the ethylene glycol would provide satisfactory purification of the bidentate compound although three contacts were most preferred since they resulted in the best americium distribution ratios.

The temperatures may vary from about 25° to 60° C. with the higher temperatures being preferred.

EXAMPLE

To illustrate the effectiveness of the ethylene glycol in washing and removing the acidic impurity from DHDECMP and DBDECMP extractants, a number of examples were run as listed in the table below. Extractants referred to as 1 and 2 in the table were prepared from typical, technical grade DHDECMP and DBDECMP, respectively, supplied by Wateree Chemical Co. The extractant designated as 3 in the table was prepared from a highly impure DHDECMP. All washing tests were performed with DHDECMP and DBDECMP compounds diluted with trichlorobenzene (TCB).

The americium distribution ratios ($D_{Am}$) at 0.1 M $HNO_3$ provides a direct measure of the amount of the acidic impurity in the bidentate extractant. Thus, the high distribution ratios for all of the unwashed extractants (particularly for extractant 3) confirm the presence of significant concentrations of the acidic contaminant in as received material. Increased temperature depresses extraction of americium by bidentate extractants. Hence, americium distribution ratios at 60° C. are slightly lower than those at 25° C. Bidentate extractants whose $D_{Am}$ at 0.1 M $HNO_3$ is less than 0.15 are found to be completely satisfactory for use in the extraction processes described hereinbefore where it is desired to use dilute $HNO_3$ media to partition the trivalent americium from co-extracted tetravalent and hexavalent actinides. Extractants with $D_{Am}$ at 0.1 M $HNO_3$ in the range 0.15 to about 0.50 can also be used in such processes but only at the expense of decreased partition and efficiency. While americium is used in the example for purposes of illustrating the same improvement in distribution ratios would be shown for any trivalent actinide.

equal-volume portions of ethylene glycol is 100 to 200-fold lower than for unwashed solvents. The efficiency of ethylene glycol washes in removing the acidic impurity is a function of the number of washes, the volume ratio of ethylene glycol to bidentate extractant, and, wash temperature. Washing at 60° C is definitely more effective than washing at 25° C. For batch-type washing, three equal volume washes at 60° C, preferably, or at 25° C are recommended. (A smaller volume ratio of ethylene glycol to bidentate extractant may be suitable in countercurrent washing equipment.) From bidentate extractants prepared from typical (e.g., Batch 1 and 2, Table I) commercially-available stock, these batch wash conditions easily produce solvents highly suitable for use in partition-type flowsheets. Even with very highly-impure DHDECMP (e.g., 20 Batch 3, Table I), three equal-volume batch ethylene glycol washes at 60° C still yield extractant which can be used in partition-type flowsheets.

It can be seen that the ethylene glycol wash procedure meets all the desiderata for a method for removing the deleterious acidic contaminant from technical-grade bidentate extractants. This wash procedure is indeed a simple, highly effective, and inexpensive purification procedure which can be routinely performed in standard stainless steel equipment. Ethylene glycol is miscible with water so disposal of spent ethylene glycol washes poses no special problems.

The embodiments of the invention in which an exclusive property or privilege is claimed are defined as follows:

1. A method for removing acidic impurities present in bidentate organophosphorus compounds comprising: diluting the organophosphorus compound selected from the group consisting of dihexyl-N,N-diethylcarbamylmethylenephosphonate and dibutyl-N,N-diethylcarbamylmethylenephosphonate with a water immiscible, organic solvent to form an extractant, contacting the extractant with ethylene glycol whereby the impuri-

TABLE I

ETHYLENE GLYCOL WASHING OF BIDENTATE ORGANOPHOSPHORUS EXTRACTANTS

Conditions: 30 volume percent DHDECMP (or DBDECMP) - TCB solvents washed as shown with ethylene glycol, americium extraction of resulting extractants determined by contacting them (either at 25° or 60° C) three times with fresh equal volume portions of 0.1 M $HNO_3$ containing ~$10^5$ μCi/liter $^{241}$Am.

| Extractant No.[β] | Wash Conditions | | | Am Distribution Ratio[α] 0.1 M $HNO_3$ | |
|---|---|---|---|---|---|
| | No. of Washes | Wash Temp. ° C | Vol. Ratio EG: Bidentate[c] | 25° C | 60° C |
| 1 | NOT WASHED | | | 11.4 | 7.88 |
|   | 1 | 25 | 1:1 | 0.937 | 0.929 |
|   | 2 | 25 | 1:1 | 0.232 | 0.212 |
|   | 3 | 25 | 1:1 | 0.109 | 0.0635 |
|   | 3 | 60 | 1:1 | 0.0621 | 0.0466 |
|   | 3 | 25 | 1:2 | — | 0.238 |
|   | 3 | 25 | 1:4 | 0.596 | — |
|   | 3 | 25 | 1:10 | 0.607 | 0.598 |
|   | 3 | 25 | 2:1 | 0.0657 | — |
| 2 | NOT WASHED | | | 4.14 | — |
|   | 3 | 25 | 1:1 | 0.0971 | — |
| 3 | NOT WASHED | | | 70.8 | 33.9 |
|   | 3 | 25 | 1:1 | 0.620 | — |
|   | 3 | 60 | 1:1 | 0.457 | 0.343 |

[α]$D_{Am}$ = Concentration Am in organic phase/Concentration Am in aqueous phase.
[β]For identification purposes only; Batches 1 and 3 DHDECMP; Batch 2 - DBDECMP.
[c]ml ethylene glycol/ml bidentate extractant.

Data in Table I clearly show that ethylene glycol washing effectively removes the offensive acidic impurity from solutions of bidentate extractants. Thus, $D_{Am}$ at 0.1 M $HNO_3$ for 30 v/o DHDECMP and DBDECMP extractants washed three times with fresh ties in the extractant are taken by the ethylene glycol, and separating the purified extractant from the ethylene glycol.

2. The method of claim 1 wherein the water immiscible organic diluent is selected from the group consisting of chlorinated hydrocarbons and long-chain aliphatic hydrocarbons.

3. The method of claim 2 wherein the water immiscible organic diluent is selected from the group consisting of carbon tetrachloride, trichlorobenzene and dodecane and contains 5 to 40 volume percent of bidentate organophosphorus compound.

4. The method of claim 3 wherein the extractant contains 30 volume percent bidentate and the volume ratio of extractant to ethylene glycol is 1:1.

5. The method of claim 4 wherein the extractant is contacted with ethylene glycol at least 3 times.

6. The method of claim 5 wherein the temperature is from about 25° to 60° C.

* * * * *